(12) United States Patent  (10) Patent No.: US 9,101,510 B2
Arnett  (45) Date of Patent: Aug. 11, 2015

(54) STERILE ADHESIVE BANDAGE WRAPPER CONSTRUCTION

(71) Applicant: Jaime Arnett, Fishers, IN (US)

(72) Inventor: Jaime Arnett, Fishers, IN (US)

( * ) Notice: Subject to any disclaimer, the term of this patent is extended or adjusted under 35 U.S.C. 154(b) by 0 days.

(21) Appl. No.: 14/271,591

(22) Filed: May 7, 2014

(65) Prior Publication Data

US 2014/0238884 A1 Aug. 28, 2014

Related U.S. Application Data

(62) Division of application No. 13/396,035, filed on Feb. 14, 2012, now Pat. No. 8,752,702.

(60) Provisional application No. 61/443,317, filed on Feb. 16, 2011.

(51) Int. Cl.
*A61B 17/06* (2006.01)
*A61F 15/00* (2006.01)

(52) U.S. Cl.
CPC ............. *A61F 15/002* (2013.01); *A61F 15/001* (2013.01)

(58) Field of Classification Search
CPC .............................. A61F 15/002; A61F 15/001
USPC ..................... 206/440, 441; 602/57
See application file for complete search history.

(56) References Cited

U.S. PATENT DOCUMENTS

| | | | | |
|---|---|---|---|---|
| 2,172,455 A * | 9/1939 | Max | ............................... | 206/441 |
| 2,245,738 A * | 6/1941 | Taylor | ............................ | 206/568 |
| 2,880,863 A * | 4/1959 | Stanton | .......................... | 206/441 |
| 2,889,039 A * | 6/1959 | Schladermundt et al. | ..... | 206/441 |
| 2,897,961 A * | 8/1959 | Bush | .............................. | 206/441 |
| 2,927,689 A * | 3/1960 | Look, Jr. | ........................ | 206/441 |
| 3,007,571 A * | 11/1961 | Marinaro | ....................... | 206/441 |
| 3,018,881 A * | 1/1962 | Wall | ............................... | 206/441 |
| 3,620,441 A * | 11/1971 | Robbins | ........................ | 229/316 |
| 3,899,077 A * | 8/1975 | Spiegelberg | ................... | 206/441 |
| 4,116,338 A * | 9/1978 | Weichselbaum | ............... | 206/438 |
| 4,235,337 A * | 11/1980 | Dotta | ............................. | 206/441 |
| 4,264,008 A * | 4/1981 | Kozlow | ......................... | 206/441 |
| 4,418,822 A * | 12/1983 | Dotta | ............................. | 206/441 |
| 4,549,653 A * | 10/1985 | Lauritzen | ...................... | 206/441 |
| 4,997,092 A * | 3/1991 | Dupont | ......................... | 206/363 |
| 5,275,284 A * | 1/1994 | Onotsky | ......................... | 206/441 |
| 5,397,297 A * | 3/1995 | Hunter | ............................ | 602/54 |
| 5,643,188 A * | 7/1997 | Oliveira | .......................... | 602/54 |

(Continued)

FOREIGN PATENT DOCUMENTS

GB 2131299 A 6/1984

*Primary Examiner* — Anthony Stashick
*Assistant Examiner* — James Way
(74) *Attorney, Agent, or Firm* — Law Office of Leo Zucker

(57) ABSTRACT

A bandage has first and second adhesive areas on corresponding end portions of the bandage for adhering the bandage to the skin of a user, and a wound dressing pad between the two adhesive areas. Portions of first and second cover strips are disposed to protect corresponding adhesive areas on the bandage. A bandage wrapper envelopes the bandage including the cover strips, and the cover strips themselves are bonded by an adhesive to a confronting surface of the wrapper. Thus, when a user pulls the ends of the wrapper apart to open the wrapper and remove the bandage, each cover strip is peeled away from the bandage by a part of the wrapper to which the cover strip is bonded. The dressing pad on the bandage is then exposed to be applied on a wound without having to come in contact with the user's hands.

10 Claims, 25 Drawing Sheets

(56) References Cited

U.S. PATENT DOCUMENTS

| | | | |
|---|---|---|---|
| 6,010,002 A * | 1/2000 | Petterson | 206/441 |
| 6,053,318 A * | 4/2000 | Petterson | 206/440 |
| 6,573,421 B1 * | 6/2003 | Lemaire | 602/57 |
| 6,719,137 B2 * | 4/2004 | Dotta | 206/441 |
| 6,855,861 B2 * | 2/2005 | Dotta | 602/57 |
| 6,923,320 B2 * | 8/2005 | Grossman | 206/440 |
| 7,591,371 B2 * | 9/2009 | Auger | 206/441 |
| 8,752,702 B2 * | 6/2014 | Arnett | 206/441 |

* cited by examiner

——— PACKAGE / WRAPPER

— — PROTECTIVE COVERS

- - - - - BANDAGE

FIG. 10
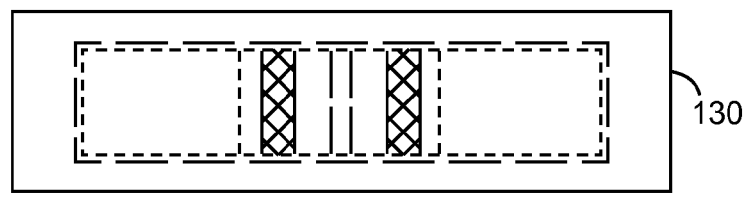
——— PACKAGE / WRAPPER
— — PROTECTIVE COVERS
- - - - - BANDAGE
 BOND AREA
FIG. 11
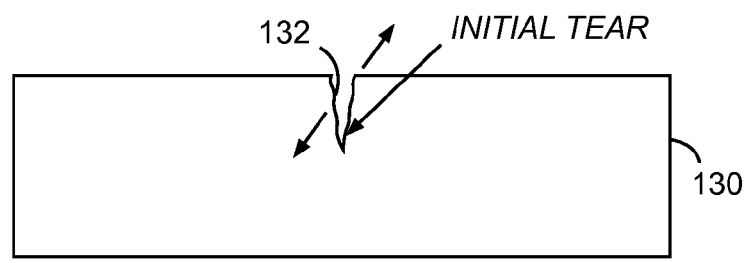

———— PACKAGE / WRAPPER

— — PROTECTIVE COVERS

------- BANDAGE

⊠⊠⊠⊠ BOND AREA

———— PACKAGE / WRAPPER

— — PROTECTIVE COVERS

------ BANDAGE

COVER PEELING BACK

MATERIAL REMOVED TO FORM NOTCHES

STRAIGHT SIDES ALLOW OPENING LOCATION VARIATION

STERILE ADHESIVE BANDAGE WRAPPER CONSTRUCTION

CROSS-REFERENCE TO RELATED APPLICATIONS

This application is a divisional under 35 U.S.C. §120 of my co-pending U.S. patent application Ser. No. 13/396,035 filed Feb. 14, 2012, which claims priority under 35 U.S.C. §119(e) of my U.S. Provisional Pat. Appl'n No. 61/443,317, filed Feb. 16, 2011. Both of the mentioned applications are incorporated herein in their entireties by reference.

BACKGROUND OF THE INVENTION

1. Field of the Invention

This invention relates to wrappers containing sterile bandages used for covering wounds or for other purposes.

2. Discussion of the Known Art

Sterile adhesive bandages are commonly used for covering skin wounds. The bandages are usually packaged in paper wrappers that are opened by separating portions of the wrapper which overlie both major sides of the bandage after tabs at the ends of the wrapper are removed, and/or by pulling a tear string. An embodiment of such a bandage wrapper is shown in FIG. 1 of the present drawing. A bandage 10 is withdrawn from its wrapper 12 by removing end tabs 14a, 14b, and peeling away cover strips 16a, 16b on the bandage 10 to expose a wound dressing pad 18 and pressure sensitive adhesive areas 20a, 20b of the bandage. The removal and preparation of the bandage 10 for application to a wound thus requires the user to have both (a) visual acuity to locate the end tabs 14a, 14b and/or tear string on the wrapper, and (b) manual dexterity to grasp and remove the tabs and to pull a tear string if also provided.

U.S. Pat. No. 7,591,371 (Sep. 22, 2009) discloses an adhesive bandage envelope having two covers of approximately the same length disposed over adhesive areas of the bandage, wherein one of the covers is folded. Further, U.S. Pat. No. 5,397,297 (Mar. 14, 1995) discloses a bandage package including covers whose lengths are intentionally different, i.e., a "short strip" and a "long strip" placed over adhesive areas of the bandage. See also UK Pat. Appl'n Pub. No. GB 2,131,299 (Jun. 20, 1984).

Notwithstanding the known art, there is a need for a compact bandage wrapper that can be opened easily and quickly to remove the bandage for use, while avoiding direct contact between a wound pad on the bandage and the user's hands, and otherwise maintaining a sterile environment.

SUMMARY OF THE INVENTION

According to the invention, an adhesive bandage wrapper construction includes a wrapper with a longitudinal edge between opposite ends of the wrapper, and a bandage inside the wrapper and having a first adhesive area on a first end portion of the bandage, a second adhesive area on a second end portion of the bandage, and a wound dressing pad between the first and the second adhesive areas. A first cover strip and a second cover strip of substantially the same length each has a protective portion disposed to protect a corresponding adhesive area on the bandage.

The wrapper envelopes the bandage including the first and the second cover strips, and the cover strips are bonded to the wrapper so that when the first and the second ends of the wrapper are pulled apart to open the wrapper and remove the bandage, each cover strip is peeled from the bandage by a part of the wrapper to which the strip is bonded. Thus, the wound dressing pad is exposed for application on a wound while direct contact between the pad and the user's hands is avoided.

For a better understanding of the invention, reference is made to the following description taken in conjunction with the accompanying drawing and the appended claims.

BRIEF DESCRIPTION OF THE DRAWING FIGURES

In the drawing:

FIG. 10 is a plan view of the inventive bandage wrapper and bandage of FIG. 9;

FIGS. 11-17 show a method of opening the bandage wrapper and removing and applying the bandage of FIGS. 9 and 10;

DETAILED DESCRIPTION OF THE INVENTION

Figure 1:
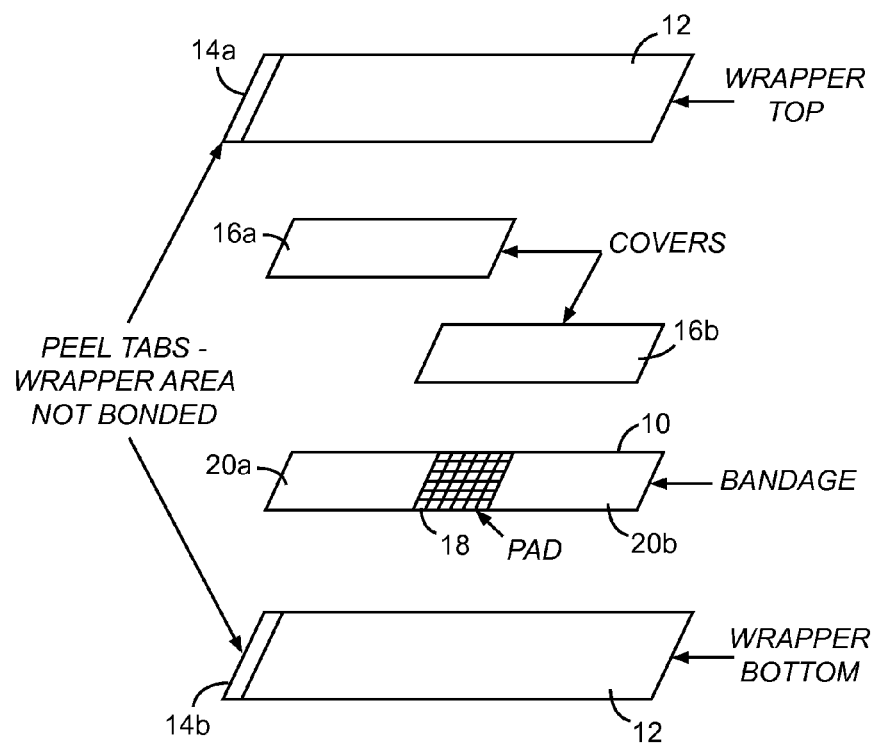
FIG. 1 is an exploded view of a conventional bandage wrapper.
Figure 2:
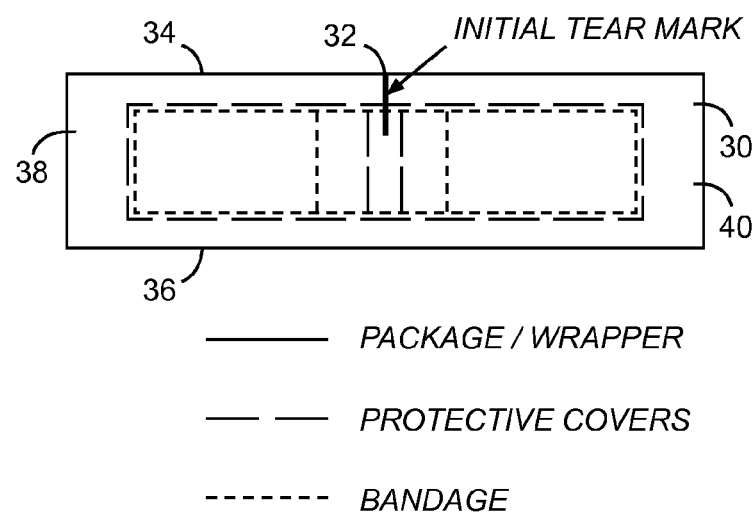
FIG. 2 is a plan view of a bandage wrapper having a slit or tear mark to facilitate opening the wrapper, and the wrapped bandage.

FIGS. 2 to 6 illustrate a bandage wrapper 30 that has a visible mark or other indicia 32 on the wrapper 30, which mark is located approximately centrally along one longitudinal edge 34 of the wrapper 30. The mark 32 indicates a position where a user is to make a short tear by hand in preparation for opening the wrapper 30. The bandage wrapper 30 may also include a second longitudinal edge 36 with a first end and a second end, a third edge 38 connecting a first end of the first longitudinal edge 34 and the first end of the second longitudinal edge 36, and a fourth edge 40 connecting the second end of the first longitudinal edge 34 and the second end of the second longitudinal edge 36. Each edge 34, 36, 38, and 40 may be continuous and straight along its entire length. In addition, the bandage wrapper 30 may be formed by a top covering portion having the edges 34, 36, 38, and 40, and a bottom covering portion having the same edges 34, 36, 38, and 40, wherein the edges 34, 36, 38, and 40 of the top covering portion are joined with the edges 34, 36, 38, and 40 of the bottom covering portion allowing for no, or substantially no, separation between the common edges 34, 36, 38, and 40 of the top and the bottom portions of the wrapper 30. The bandage wrapper 30 may therefore omit end peels or pull apart tabs such as are provided on existing bandage wrappers and which are usually about 3-5 millimeters wide.

Figure 3:
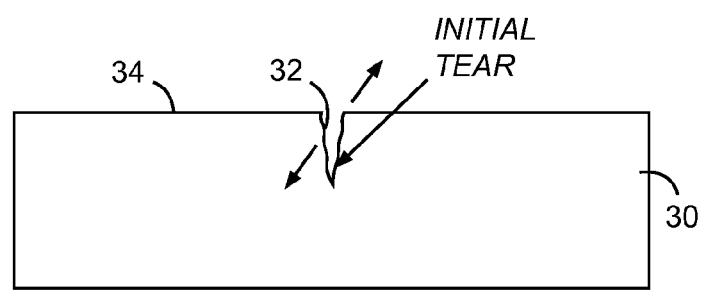
FIGS. 3-8 show opening of the wrapper of FIG. 2, and removing and applying the bandage.
Figure 4:
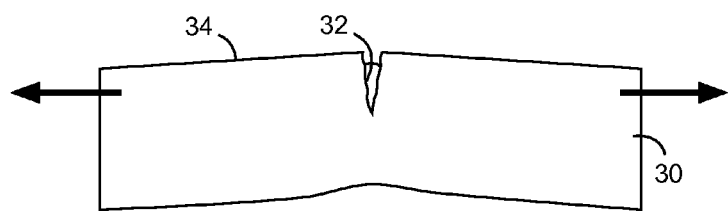
Figure 5:
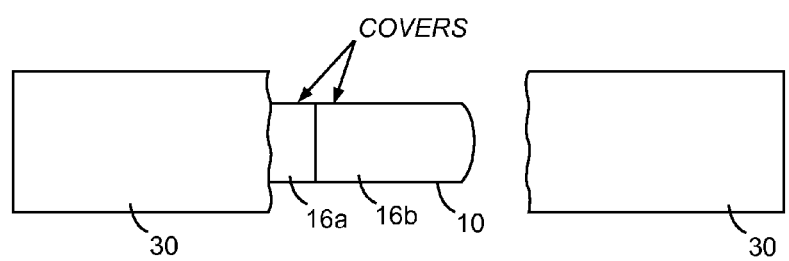
Figure 6:
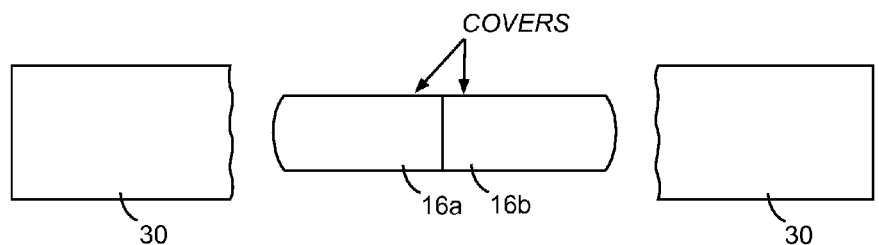
Figure 7:
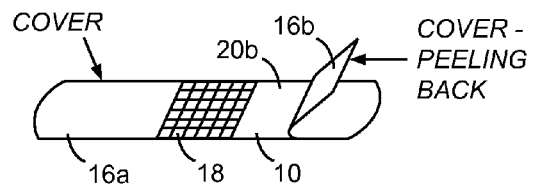
Figure 8:
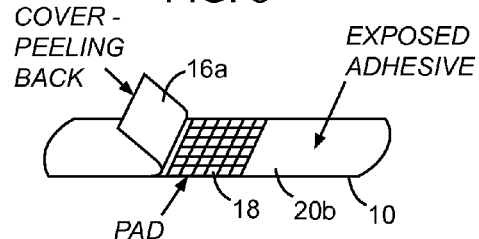

As shown in FIGS. 3-4, after a user makes a tear at the mark 32, the bandage wrapper 30 is grasped at opposite ends of the long edge 34 and pulled apart. As shown in FIG. 4, the user may grasp the bandage wrapper 30 beyond the areas covering the bandage 10 in order to avoid pinching the bandage 10 while tension is applied to the wrapper 30. Once the wrapper 30 is fully separated in two, as shown in FIGS. 5-6, a portion of the bandage 10 is exposed and the rest of the bandage can be removed from the separated wrapper 30. As shown in FIGS. 7-8, cover strips 16a, 16b are peeled away to expose the wound dressing pad 18 and the pressure sensitive adhesive areas 20a, 20b of the bandage 10.

It has been discovered that after making a short tear by hand at the mark 32, the tension needed to pull the bandage wrapper 30 apart enough to remove the bandage 10 is significantly and unexpectedly less than that required if a slit or notch is pre-cut in the vicinity of the mark 32. The wrapper 30 of FIG. 2 can be manufactured in a manner the same or similar to that used to make the wrapper of FIG. 1, with an additional step of providing the mark 32 on the wrapper 30 to show the user where he or she should tear and then pull the wrapper apart in order to remove the bandage 10. As mentioned, the end tabs 14a, 14b provided on the existing wrappers 12 may be eliminated saving both material and manufacturing costs.

Figure 9:
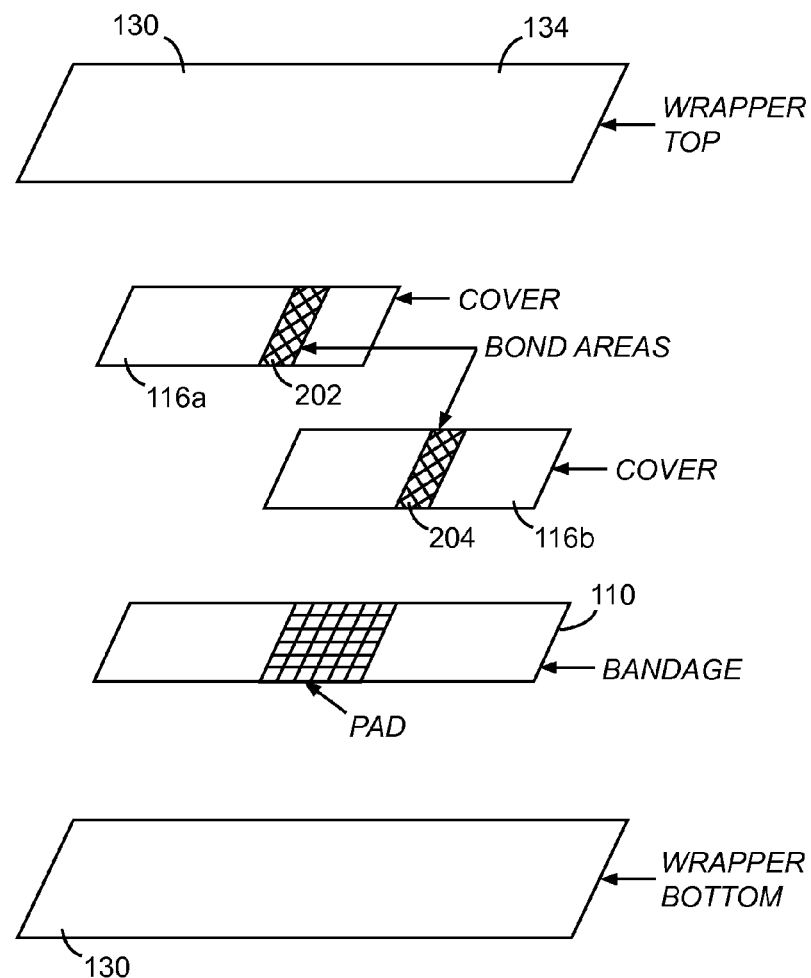
FIG. 9 is an exploded view of an embodiment of a bandage wrapper and bandage according to the invention.
Figure 12:
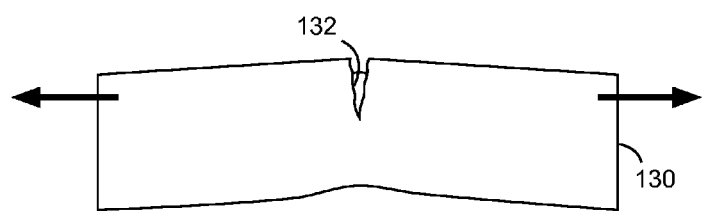

FIGS. 9 to 17 illustrate an embodiment of the present invention. A bandage wrapper 130 includes some elements that may be the same or similar to elements of the wrapper 30 shown in FIGS. 2 to 8. As shown in FIGS. 9-11, the wrapper 130 includes a longitudinal edge 134 with a first end and a second end, the longitudinal edge 134 being continuous and straight from the first end to the second end. The wrapper 130 enables the cover strips 116a, 116b to be removed automatically when the wrapper 130 is separated from the bandage 110 after the user makes an initial tear at the mark 132 and pulls the wrapper apart. Adhesive bonding areas 202, 204 are provided on outwardly facing surfaces of the cover strips 116a, 116b so that the strips will also adhere to the confronting, inwardly facing surface of the wrapper 130. The bonding areas 202, 204 should be spaced from one another enough to ensure that the wrapper 130 will tear and separate in the region between the bonding areas, and that both cover strips 116a, 116b will peel away from the bandage 110 as the separated portions of the wrapper 130 are removed. The bonding areas 202, 204 may, e.g., be thin and rectangular shaped. In addition, the bonding areas 202, 204 may extend in a transverse direction, i.e., across the width of each cover strip 116a, 116b.

The adhesive bond areas 202, 204 of this embodiment may include, for example, pressure-sensitive adhesives (rubbers, acrylate and silicone formulations), dissolvable adhesives, removable adhesives, reactive adhesives, drying adhesives, contact adhesives, light-curing adhesives, thermoplastic adhesives, synthetic adhesives (acrylics, cynoacrylates, silicone, polyurethane), biological adhesives, or any other suitable adhesive known in the art.

Figure 13:
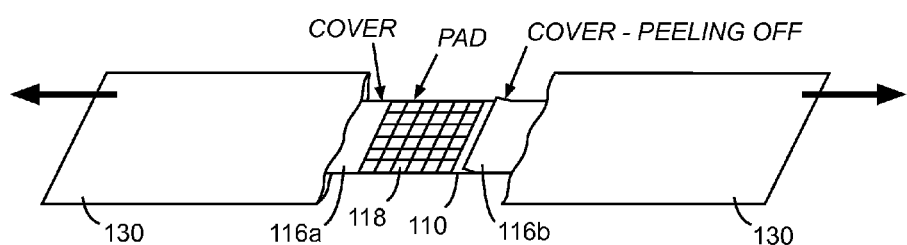
Figure 14:
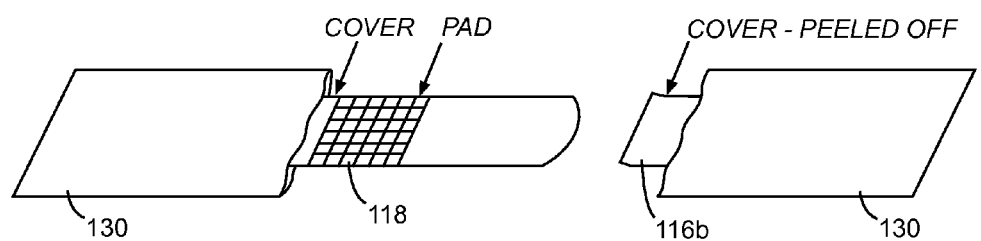
Figure 15:
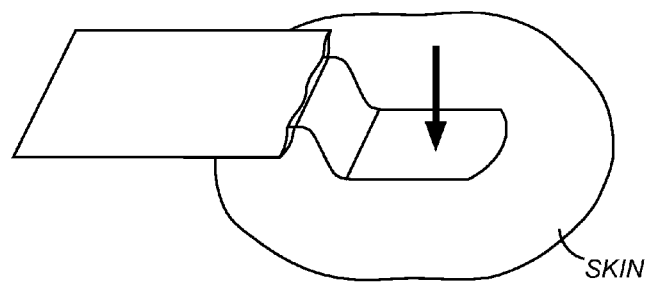
Figure 16:
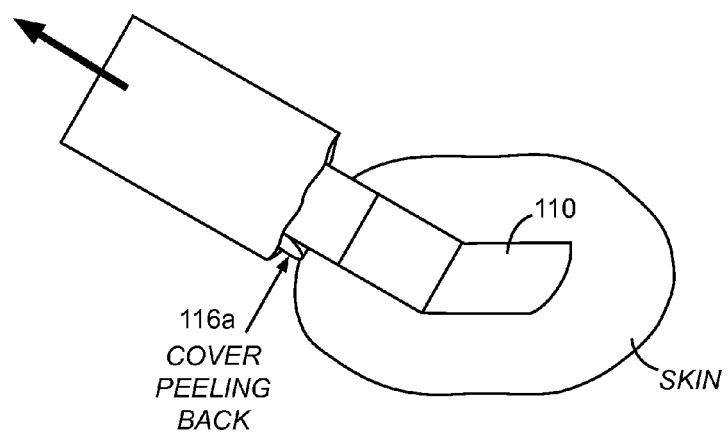
Figure 17:
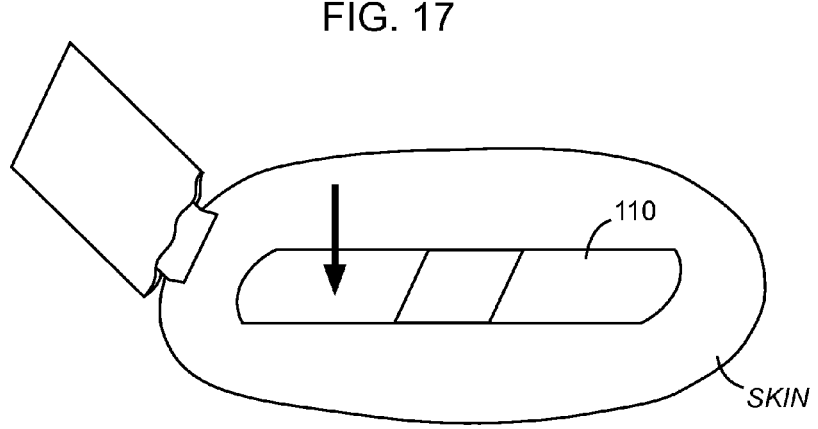

FIG. 10 is a plan view of the bandage wrapper 130, and FIGS. 11 to 17 show a progression of removing the bandage 110 from the wrapper 130 and applying the bandage 110 to the skin. According to one aspect of this embodiment as shown in FIG. 13, after a user makes the initial tear, the opposite ends of the wrapper 130 are pulled apart to separate the wrapper 130 into left and right halves. Then, only one half, (e.g., the right half in FIG. 13), is pulled off of the bandage 110 so as to peel the cover strip 116b away from the pressure sensitive part of the right side of the bandage 110. As shown in FIG. 15, with the pressure sensitive adhesive at the right side of the bandage 110 exposed, the user applies the exposed right side of the bandage 110 adjacent to the wound. Then, in FIG. 16, the left half of the wrapper 130 is pulled off of the bandage 110 so as to peel the cover strip 116a away from the pressure sensitive part of the left side of the bandage. As shown in FIG. 17, with the pressure sensitive adhesive at the left side of the bandage 110 exposed, the user applies the wound dressing pad on the wound, and the exposed left side of the bandage 110 is applied adjacent the wound opposite the right side of the bandage. It will be appreciated that with this embodiment, direct contact with the wound by the user is easily avoided over the entire process of removing and applying the bandage, thus providing for a more sterile application of the bandage.

Figure 18:
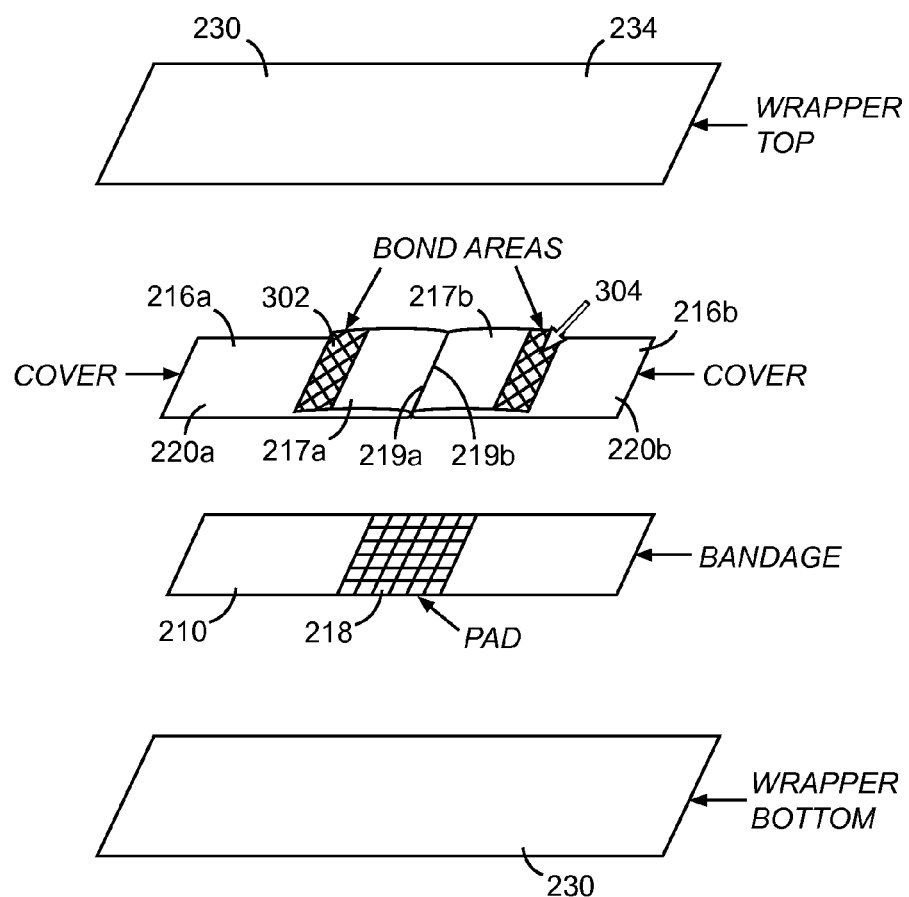
FIG. 18 is an exploded view of another embodiment of a bandage wrapper and bandage according to the invention.
Figure 19:
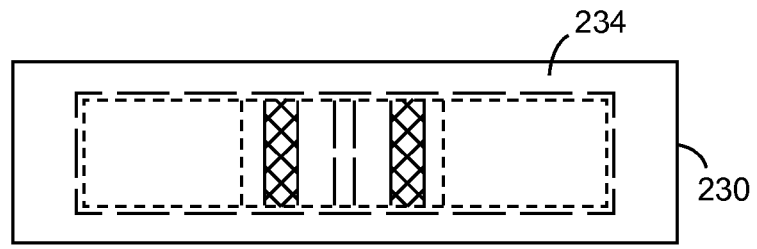
FIG. 19 is a plan view of the inventive bandage wrapper and bandage of FIG. 18.
Figure 20:
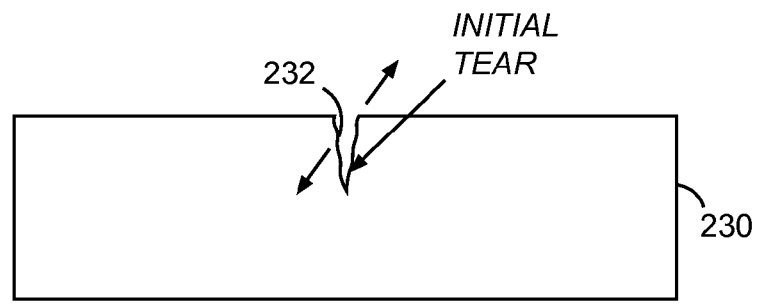
FIGS. 20-26 show a method of opening the bandage wrapper, and of removing and applying the bandage of FIGS. 18 and 19.

FIGS. 18 to 26 illustrate another embodiment of the invention, wherein a bandage wrapper 230 includes some elements that may be the same or similar to elements of the wrapper 30 shown in FIGS. 2 to 8. As seen in FIGS. 18 and 19, the wrapper 230 includes a longitudinal edge 234 with a first end and a second end, the longitudinal edge 234 being continuous and straight from the first end to the second end. The wrapper 230 also features automatic removal or peeling away of protective cover strips 216a, 216b as the wrapper is separated from the bandage 210. Each cover strip 216a, 216b has an overlapping folded portion 217a, 217b, and an adhesive bonding area 302, 304 is applied on each of the folded portions 217a, 217b.

In addition to the overlapping folded portions 217a, 217b, and the adhesive bonding areas 302, 304, each cover strip 216a, 216b may also include a fold 219a, 219b and a cover portion 220a, 220b, the cover portion 220a, 220b covering the adhesive of the bandage 210 and a portion of the pad 218 of the bandage 210. In addition, the overlapping folded portion 217a, 217b is sandwiched between the wrapper 230 and the cover portion 220a, 220b.

Accordingly, less force would be needed to separate the left and the right halves of the wrapper 230 after making the initial tear and removing the cover strips 216a, 216b, than the force needed to separate the wrapper 130 and remove the cover strips 116a, 116b in the embodiment of FIGS. 9 to 17. As in the embodiment of FIGS. 9 to 17, there should be enough space between the bonding areas 302, 304 to ensure the wrapper 230 will tear fully between the bonding areas, and that both cover strips 216a, 216b will peel away as each half of the wrapper 230 is separated and withdrawn from the bandage 210. The bonding areas 302, 304 may be thin and rectangular shaped, and extend in a transverse direction, i.e., across the width of each cover strip 216a, 216b as shown. The adhesive bonding areas 302, 304 are preferably located at the free ends of each folded portion 217a, 217b, and on the upper side of each folded portion 217a, 217b as shown in the drawing.

The upper side of each folded portion 217a, 217b of the cover strips 216a, 216b, is approximately one-half the length of the underside portion of the corresponding strip 216a, 216b. In addition, the folded portions 217a, 217b may slightly overlap with one another in the vicinity of their respective folds 219a, 219b.

The adhesive bond areas 302, 304 of this embodiment may include, for example, pressure-sensitive adhesives (rubbers, acrylate and silicone formulations), dissolvable adhesives, removable adhesives, reactive adhesives, drying adhesives, contact adhesives, light-curing adhesives, thermoplastic adhesives, synthetic adhesives (acrylics, cynoacrylates, silicone, polyurethane), biological adhesives, or any other suitable adhesive known in the art.

It is known in the manufacturing art of some bandages to attach protective cover strips to the adhesive portions of the bandages, and then to cut out individual bandages with associated cover strips simultaneously using the same cutting die. The embodiments described above will allow the bandages 110, 210 and their associated cover strips 116a, 116b, and 216a, 216b, to be cut by the same die simultaneously thus helping to save material and manufacturing costs.

Figure 21:
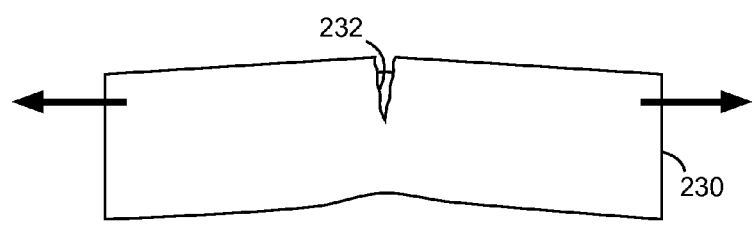
Figure 22:
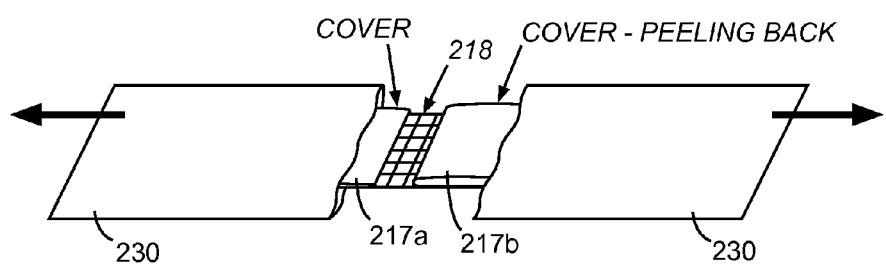
Figure 23:
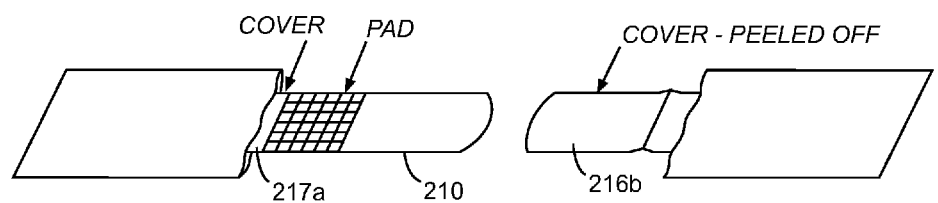
Figure 24:
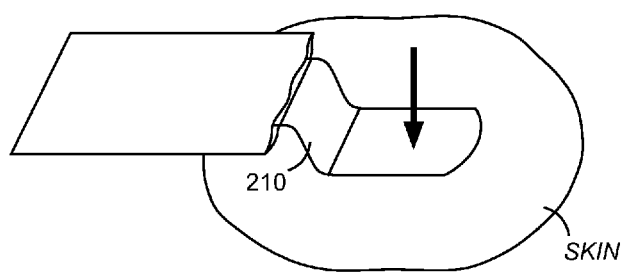
Figure 25:
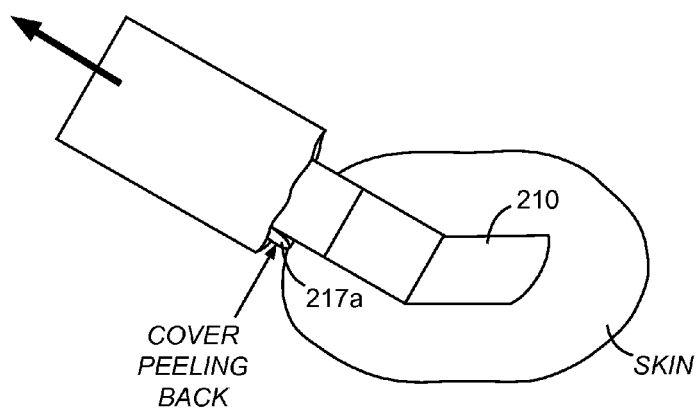
Figure 26:
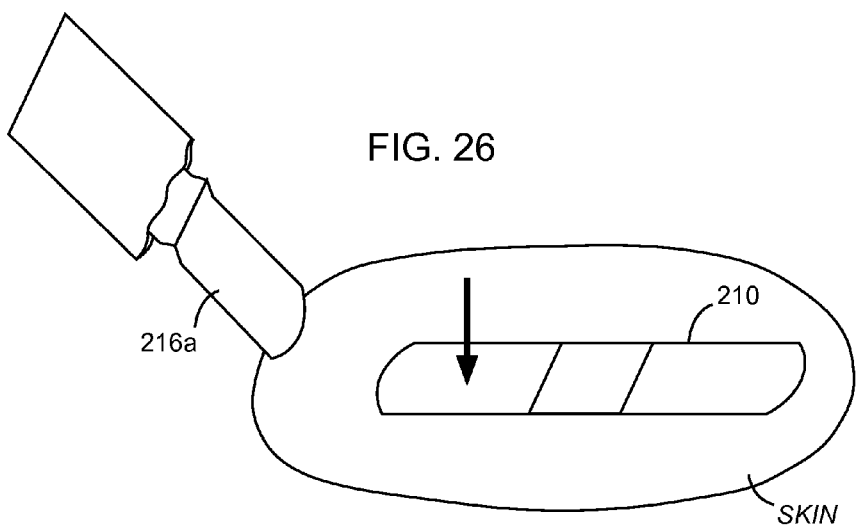

FIGS. 20 to 26 show a progression of opening the wrapper 230, and removing and applying the bandage 210. As seen in FIGS. 21-23, after the wrapper 230 is fully torn, the right half of the wrapper 230 is withdrawn and the protective cover strip 216b at the right side of the bandage 210 is peeled away to expose the pressure sensitive adhesive on the bandage. As shown in FIG. 24, this allows the user to apply the exposed (right) side of the bandage 210 adjacent to the wound. Then, in FIGS. 25-26, the left half of the wrapper 230 is withdrawn from the bandage 210 causing the cover strip 216a at the left side of the bandage to be peeled away, and allowing the user to apply the bandage dressing pad 218 over the wound and the exposed pressure sensitive adhesive of the bandage next to the wound. It will be appreciated that this avoids any direct contact by the user with the wound dressing pad during the entire process of opening the wrapper 230, and removing and applying the bandage 210, thereby providing for a more sterile application of the bandage.

Figure 27:
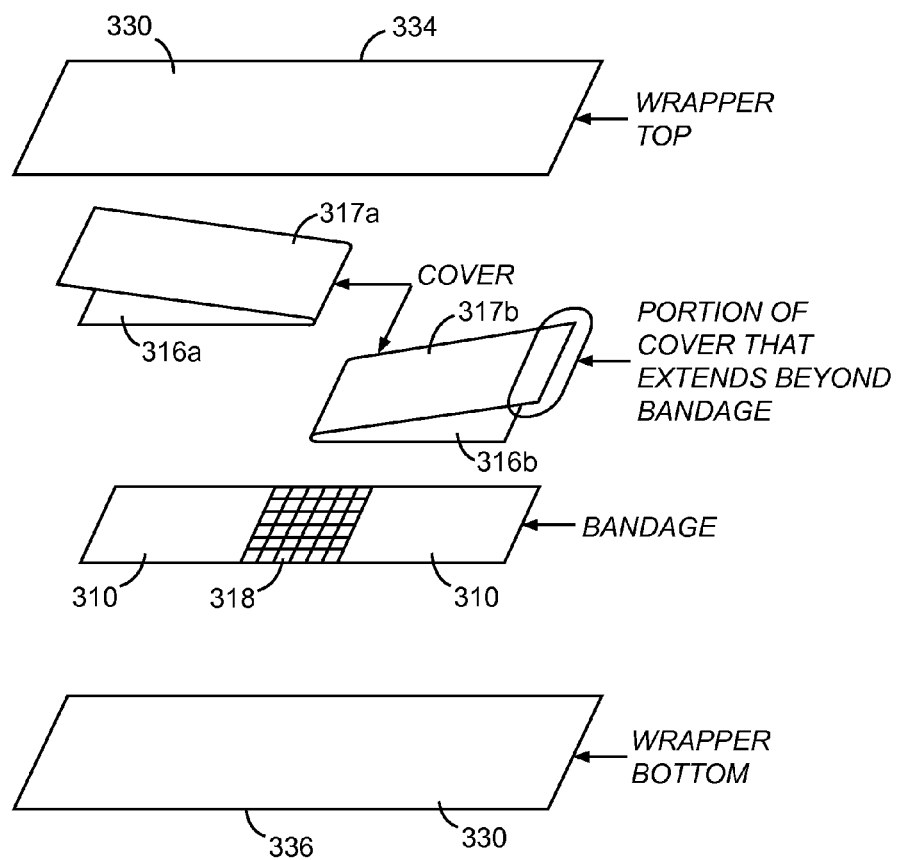
FIG. 27 is an exploded view of another embodiment of a bandage wrapper and bandage.
Figure 28:
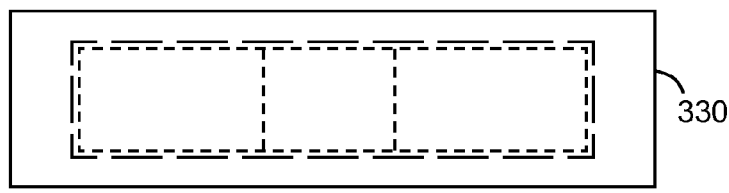
FIG. 28 is a plan view of the bandage wrapper and bandage of FIG. 27.
Figure 29:
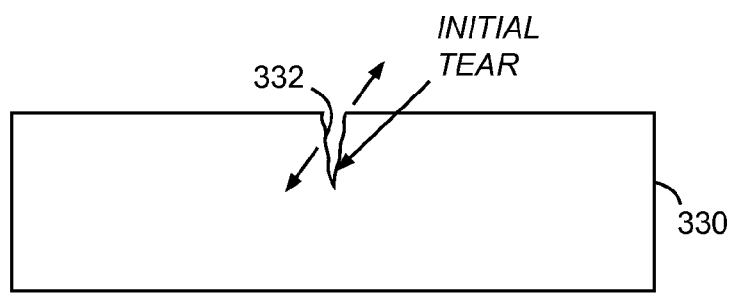
FIGS. 29-35 show a method of opening the bandage wrapper and removing and applying the bandage of FIGS. 27 and 28.
Figure 30:
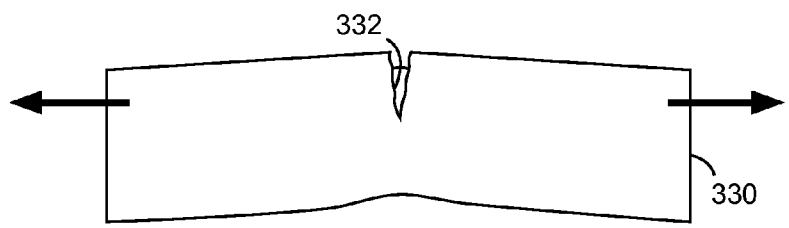
Figure 31:
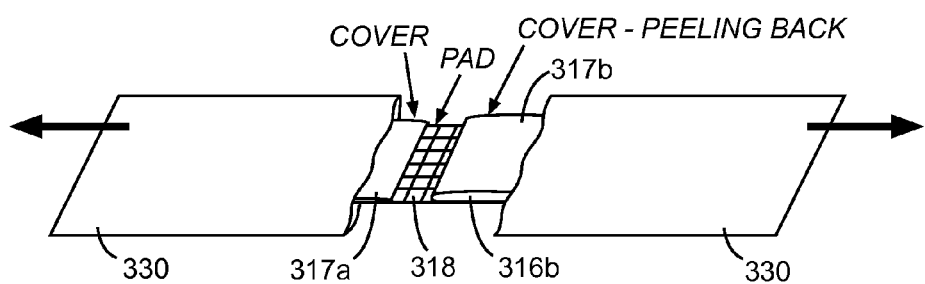
Figure 32:
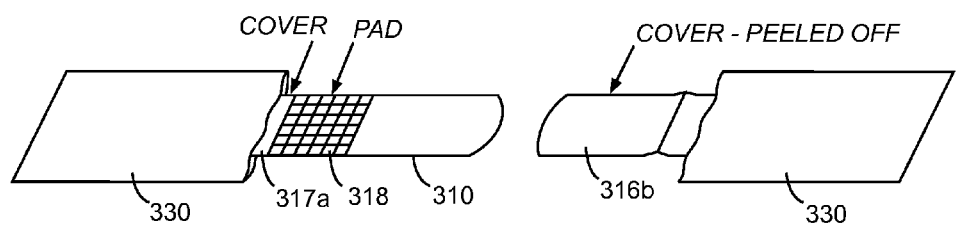
Figure 33:
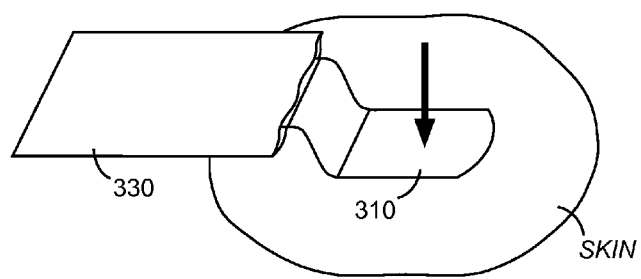
Figure 34:
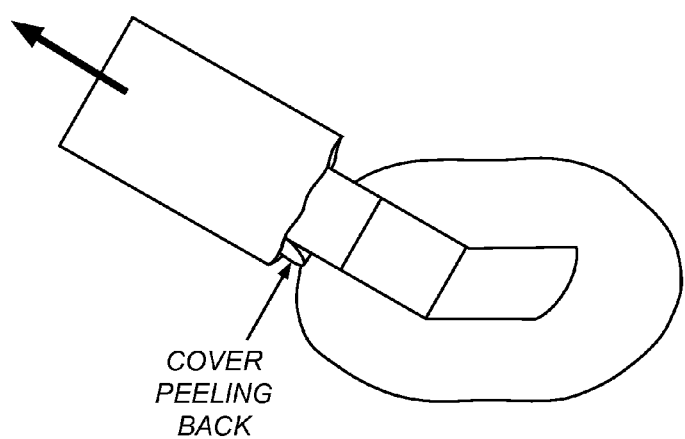
Figure 35:
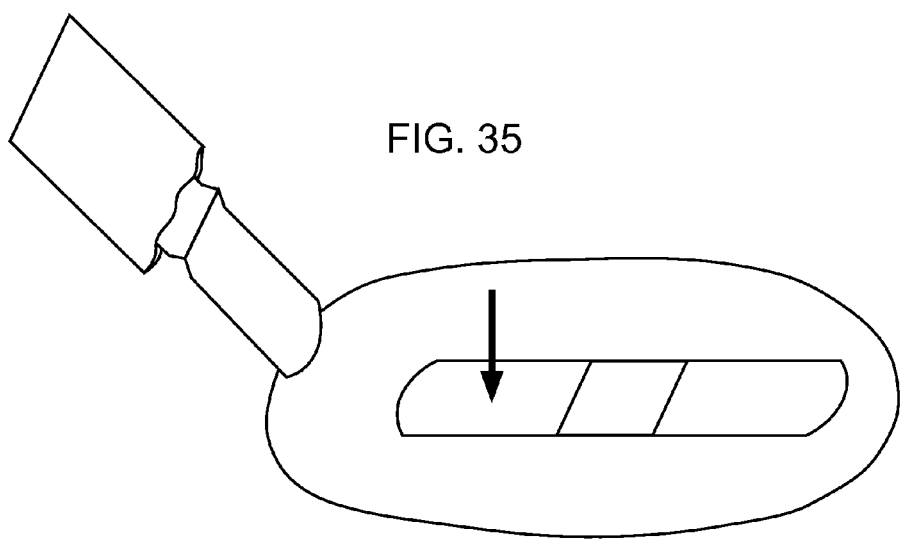

FIGS. 27 to 35 illustrate another embodiment, wherein a bandage wrapper 330 includes elements that may be the same or similar to elements of the wrapper 30 shown in FIGS. 2 to 8. In FIGS. 27 to 28, the wrapper 330 includes a longitudinal edge 334 with a first end and a second end, the longitudinal edge 334 being continuous and straight from the first end to the second end. The wrapper 330 also features automatic removal of protective cover strips 316a, 316b from the pressure sensitive adhesive areas of the bandage 310 when the wrapper 330 is removed. The cover strips 316a, 316b have folded portions 317a, 317b, each folded portion having an end which extends beyond the opposite ends of the adhesive portions of the bandage 310. As the left and the right halves of the wrapper 330 are grasped and separated after making the initial tear, the extended ends of the cover strip portions 317a, 317b are pinched between the top and the bottom sides of the wrapper 330. As the halves of the wrapper 330 are separated from the bandage 310, the cover strips 316a, 316b are then peeled away from the bandage 310.

FIGS. 29 to 35 show a progression of opening the wrapper 330, and removing and applying the bandage 310. In FIGS. 30-33, as the right half of the wrapper 330 is withdrawn, the right protective strip 316b automatically peels away to expose the pressure sensitive adhesive on the right side of the bandage. It will be appreciated that this allows the user at once to apply the exposed right side of the bandage adjacent to the wound area. Then, in FIGS. 34 and 35, the left half of the wrapper is withdrawn, thus allowing the user to apply the wound dressing pad over the wound, and to apply the exposed adhesive area at the left side of the bandage next to the wound area. It will be appreciated that during this process, the user also avoids direct contact with the wound dressing pad for a more sterile application of the bandage.

Instead of requiring the user to make an initial tear at a pre-printed tear mark or other indicia on the bandage wrapper, the wrapper may be produced with a pre-cut slit or notch in the same region of the wrapper. While this would eliminate the need for the user to make the initial tear by hand, it would require an additional manufacturing step to cut the slit or notch, and a sufficient area of the wrapper must extend beyond the perimeter of the bandage to ensure that the bandage is properly sealed before use. The slitting or notching step may be incorporated with existing bandage wrapper slitting operations, wherein it is common for bandages to be produced from large sheets which are slit apart to form individual bandages or strips of bandages. For example, FIGS. 36 to 46 show various embodiments of slit and notch arrangements according to the present disclosure.

Figure 36:
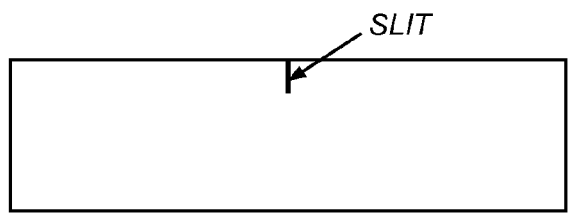
FIGS. 36 to 46 show embodiments of bandage wrappers having slits, notches, or tear marks to facilitate opening the wrapper according to the invention.
Figure 37:
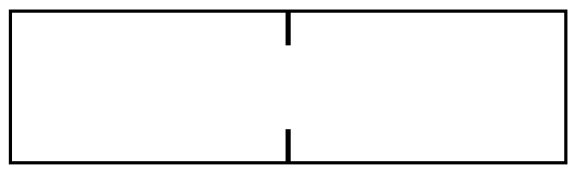
Figure 38:
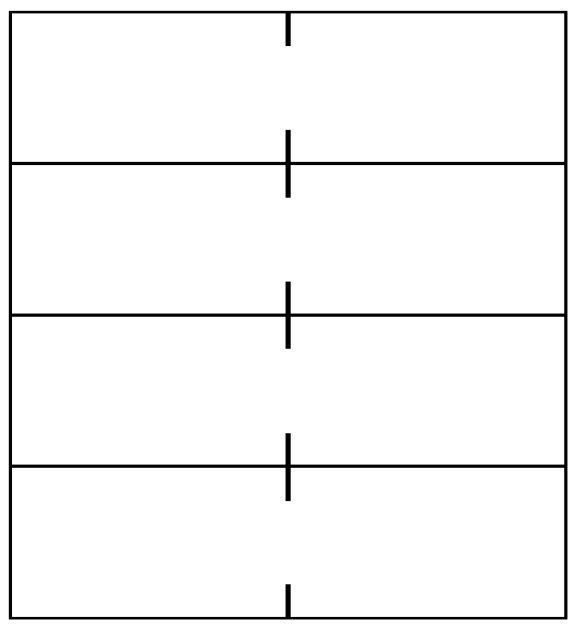

FIGS. 36 to 38 illustrate embodiments of a slit and notch arrangement. As shown in FIG. 36, a first slit may be located in a central location of the bandage wrapper and extend in a downward transverse direction from a top edge across a portion of the width of the bandage wrapper. And as seen in FIGS. 37 and 38, the bandage wrapper may include a second slit located opposite the first slit. The second slit may extend in an upward transverse direction from a bottom edge, i.e., across a portion of the width of the bandage wrapper.

Figure 39:
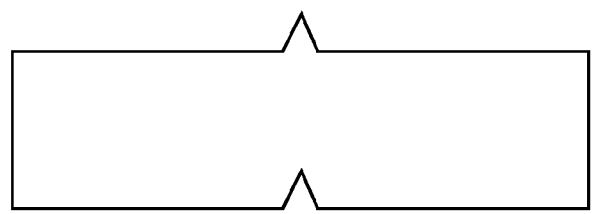
Figure 40:
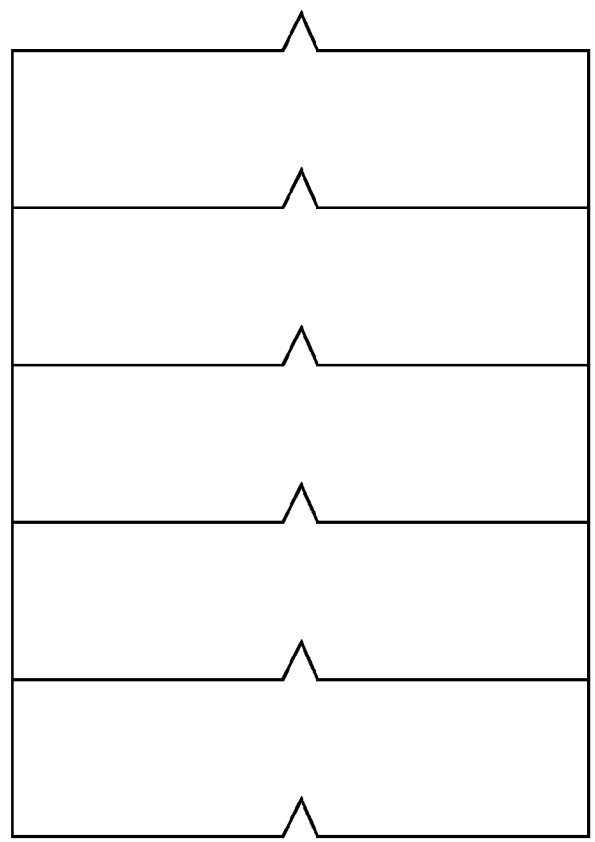

FIGS. 39 and 40 illustrate further embodiments of slit and notch arrangements. As shown, the slit or notch may include a triangular protrusion at a top edge of the bandage wrapper and a triangular notch located at the bottom edge of the bandage wrapper.

Figure 41:
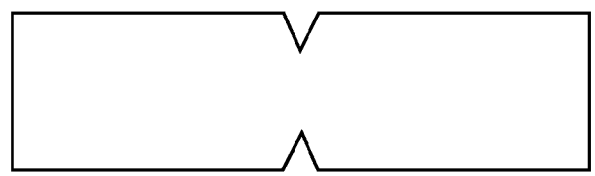
Figure 42:
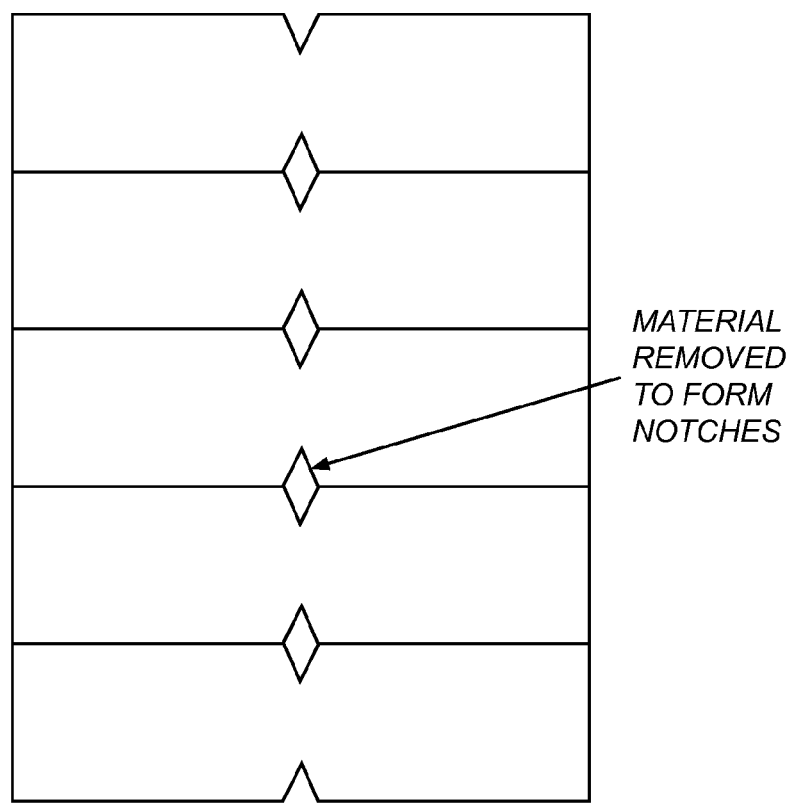

FIGS. 41 and 42 illustrate other embodiments of slit and notch arrangements wherein the slit or notch may include an inwardly protruding triangular shaped notch at a top edge of the bandage wrapper, and an inwardly protruding triangular shaped notch located at the bottom edge of the bandage wrapper.

Figure 43:
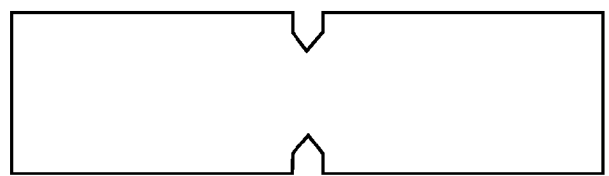
Figure 44:
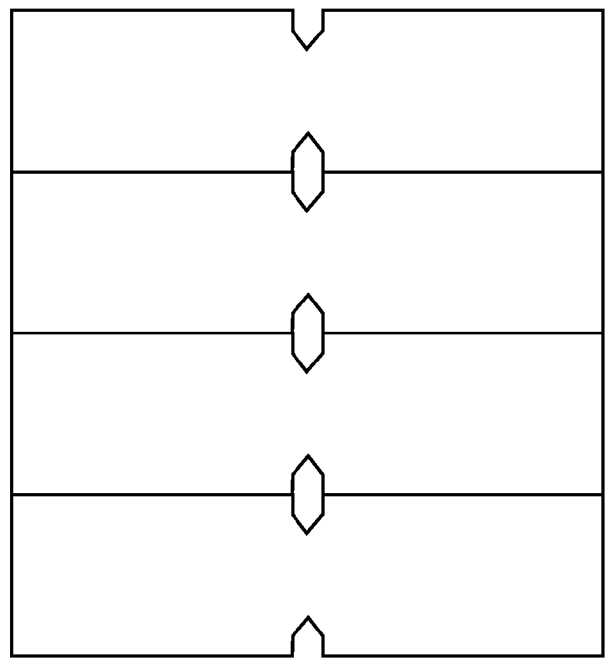
Figure 45:

FIGS. 43 to 45 illustrate further embodiments of slit and notch arrangements wherein the slit or notch may include an inwardly protruding half diamond shaped notch, including two straight sides, at a top edge of the bandage wrapper and an inwardly protruding half diamond shaped notch, including two straight sides, located at the bottom edge of the bandage wrapper.

Figure 46:
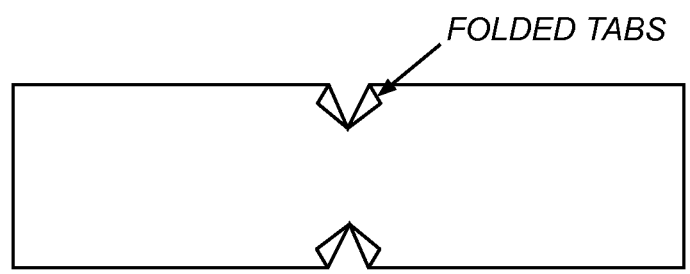

FIG. 46 illustrates another embodiment of a slit and notch arrangement wherein the slit or notch may include an inwardly protruding notch, with folded tabs, at a top edge of the bandage wrapper and an inwardly protruding notch, including folded tabs, located at the bottom edge of the bandage wrapper.

Simple graphics are typically printed on bandage wrappers or packaging to illustrate how the wrappers are to be removed. In the embodiments of the present invention, various graphics can also be printed or displayed on the bandage wrappers in order to convey corresponding instructions for opening the wrappers. For example, as shown in FIG. 11, a "tear" graphic may be printed at the location on the wrapper where the user makes an initial tear by hand.

The disclosed embodiments of the present invention may be produced using the same or similar methods as currently used in the manufacture of wrapped sterile bandages. That is, no major modifications or replacements of existing manufacturing equipment is required. Having the user make the initial tear in the wrapper allows the wrapper to remain the same size as existing bandage wrappers, so that no additional wrapper material needs to be consumed beyond that used in the production of the existing bandage wrappers.

According to various embodiments of the present disclosure, the following advantages are also obtained by having the user make the initial tear by hand, rather than providing the wrapper with a pre-cut tear or notch.

1. Less outer wrapper material is required for the hand tear wrapper. Since the perimeter of the wrapper must be sealed to maintain sterility of the bandage, more wrapper material would be needed if the width of the sealed region is to be maintained.

2. A precise cut would be needed in production so that the cut does not encroach into the sealed region of the wrapper, and the cut penetrates the wrapper material enough to allow the user to start to separate the wrapper.

3. It has been discovered that the wrapper can be opened and separated using significantly less force when making the initial tear by hand, when compared to the force needed to separate and open a wrapper having a cut (see the data in Tables 1, 2 and 3, below). This allows a larger population to use the inventive wrappers and the bandages contained therein successfully.

In addition, according to various embodiments of the present invention, the bandage wrapper does not require use of peel-apart tabs and, consequently, there will be a savings of material resulting from the elimination of the tabs. This includes the wrapper paper, adhesive, and ink. The savings resulting from elimination of the tabs is significant and can range between 5 and 18% depending on the bandage.

Furthermore, for some currently available bandage wrappers, the peel tabs are made by folding over the end of the wrapper strip. According to various embodiments of the present invention, this folding operation would also be eliminated.

Also, reducing the amount of materials used benefits the environment by requiring less energy to make the raw materials and reduction of inherent by-products of the manufacturing processes.

In addition, there is a potential savings for the adhesive that is used to attach the wrapper halves. Since the adhesive does not need to be pulled apart, a less expensive adhesive may be suitable.

Also, some current arrangements of bandages and wrappers require tearing the wrapper on one side or the other of the gauze pad, instead of near the center of the bandage. If not torn at the pad region near the center of the bandage, some current bandages are susceptible to tearing of the adhesive coated flexible portion of the bandage that is intended to adhere to the skin.

Figure 47:
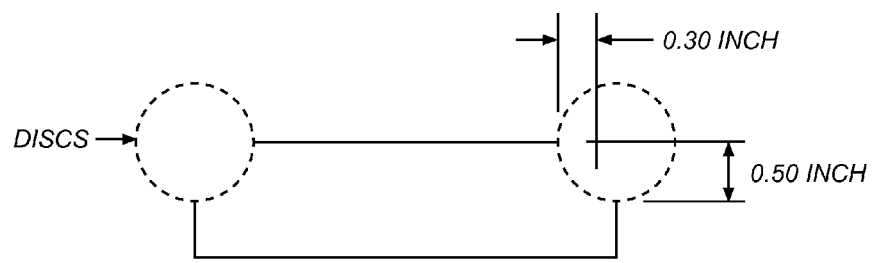
FIGS. 47 and 48 illustrate a method of determining forces needed to open fully bandage wrappers with partial cuts or tears.

Wrapped bandages from three major manufacturers (Band-aid, Nexcare, and Royal) were tested to determine the force required to shear the wrappers apart in order to expose the wrapped bandages. The opposite ends of each wrapper were gripped by elastomer discs to simulate grasping by a user's fingers. FIG. 47 shows the location of the grips, representing the preferred grasping locations.

Figure 48:
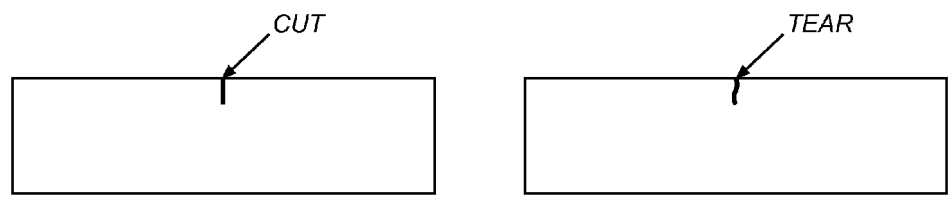

The tests evaluated the separation forces needed for bandage wrappers having a clean cut versus a hand tear to start the wrapper separation. The cuts and the tears were located at the center of one long edge of the bandage wrapper. The cut lengths were ⅛ inch and 3/16 inch long, starting at the wrapper edge toward the center of the bandage. The hand tear was made from the wrapper edge and extended to and sometimes slightly past the bandage. As shown in FIG. 48, tearing to the edge of the bandage is a very natural motion.

It is important to note that there is a tradeoff in determining the length of the cut. The cut needs to be long enough to function as a point of stress concentration. Generally, based on additional testing, the longer the cut the easier it is to shear the wrapper. There is also a desire to minimize the length of the cut, however, because the wrapper must increase in width by an amount equal to the length of the cut in order to maintain a sterile seal around the perimeter of the bandage.

TABLE 1

Separation Force testing of "Band-Aid" Brand Bandages

| Model | Size (inch) | Start | Sample size | Average (lbs) | Standard Deviation (lbs) |
| --- | --- | --- | --- | --- | --- |
| Plastic Strip | ¾ × 3 | ⅛" cut | 30 | 6.1 | 0.91 |
| Plastic Strip | ¾ × 3 | 3/16" cut | 10 | 4.33 | 0.96 |
| Plastic Strip | ¾ × 3 | tear | 30 | 2.67 | 0.5 |
| Plastic Strip | ⅝ × 2¼ | ⅛" cut | 10 | 6.15 | 0.5 |
| Plastic Strip | ⅝ × 2¼ | 3/16" cut | 10 | 5.17 | 0.85 |
| Plastic Strip | ⅝ × 2¼ | tear | 10 | 2.68 | 0.41 |
| Sport Strip | 1 × 3 3/16" | cut | 10 | 5.49 | 0.87 |
| Sport Strip | 1 × 3 | tear | 10 | 3.41 | 0.63 |
| Antibiotic | ¾ × 3⅛" | cut | 10 | 13.4 | 1.1 |
| Antibiotic | ¾ × 3 | tear | 31 | 6.1 | 0.91 |
| Antibiotic | ⅝ × 2¼ | ⅛" cut | 9 | 11.6 | 1.34 |
| Antibiotic | ⅝ × 2¼ | tear | 9 | 7.4 | 1.1 |

The overall weighted average for Band-Aid bandages with Tear/Cut ⅛"=49.5%. The overall weighted average for Band-Aid bandages with Tear/Cut 3/16"=56%. These percentages illustrate the weighted average of the amount of force required for a user to pull apart a tear vs. the amount of force required for a user to pull apart a cut.

TABLE 2

Separation Force testing of "Nexcare" Brand Bandages

| Model | Size (inch) | Start | Sample size | Average (lbs) | Standard Deviation (lbs) |
| --- | --- | --- | --- | --- | --- |
| Heavy Duty Flex Fabric | ¾ × 3 | 3/32* cut | 10 | 9.1 | 1.13 |
| Heavy Duty Flex Fabric | ¾ × 3 | tear | 30 | 2.7 | 0.71 |
| Comfort Fabric | ¾ × 3 | ⅛" cut | 10 | 6.7 | 0.91 |
| Comfort Fabric | ¾ × 3 | tear | 25 | 3.2 | 0.66 |

*border width was not sufficient for ⅛" cut

The average for Nexcare bandages of Tear/Cut 3/32"=63%. The overall weighted average for Nexcare bandages of Tear/Cut ⅛"=48%. These percentages illustrate the weighted average of the amount of force required for a user to pull apart a tear vs. the amount of force required for a user to pull apart a cut.

TABLE 3

Separation Force testing of "Royal" Brand Bandages

| Model | Size (inch) | Start | Sample size | Average (lbs) | Standard Deviation (lbs) |
| --- | --- | --- | --- | --- | --- |
| Flex Fabric | ¾ × 3 | ⅛" cut | 10 | 1.86 | 0.58 |
| Flex Fabric | ¾ × 3 | tear | 10 | 1.20 | 0.25 |

The average for Royal bandages with Tear/Cut ⅛"=0.65%. The Tear/Cut ratios below each table show that there is a significant advantage to using a hand tear to start the wrapper separation compared to a cut. This percentage illustrates the weighted average of the amount of force required for a user to pull apart a tear vs. the amount of force required for a user to pull apart a cut.

As disclosed herein, the inventive bandage wrapper can be opened, and the bandage contained therein removed and applied to a wound in a sterile manner and in significantly less time compared with existing wrappers.

While the foregoing represents preferred embodiments of the present invention, it will be understood by persons skilled in the art that various changes, modifications, and additions can be made without departing from the spirit and scope of the invention.

For example, while the adhesive bandages are shown herein in a particular form intended to cover skin wounds, the bandages may also be, but are not limited to, strip bandages, winged bandages, fingertip bandages, butterfly bandages, knuckle bandages, triangular bandages, tube bandages, compression bandages, elastic bandages, gauze bandages, donut bandages, pressure bandages, steristrips, eye bandages, sterile burn sheets, and adhesive tape.

Further, the wrappers described herein may also be used to package other strip-like products, including, for example, strips for relieving nasal congestion or skin irritation, or for treating various other ailments by applying the products to the skin. Accordingly, the invention includes all such changes, modifications, and additions that are within the scope of the following claims.

I claim:

1. An adhesive bandage wrapper construction, comprising:
    a wrapper having a longitudinal edge between a first end and a second end of the wrapper;
    a bandage contained in the wrapper and including first and second adhesive areas on corresponding end portions of the bandage for adhering the bandage to a user's skin, and a wound dressing pad disposed between the first and the second adhesive areas of the bandage for application on a wound of the user;
    a first cover strip and a second cover strip, wherein the cover strips are of substantially the same length, and each cover strip has a protective portion dimensioned and arranged to adhere to and to protect a corresponding adhesive area on the bandage, and a relatively thin bond area on a side of the cover strip that faces away from the corresponding adhesive area of the bandage and intermediate the wound dressing pad and the corresponding end of the wrapper, wherein the bond area includes an adhesive disposed across the width of the cover strip between the wound dressing pad and a free end of the cover strip; and
    wherein the wrapper envelopes the bandage including the first and the second cover strips, and the sides of the cover strips that face away from the adhesive areas of the bandage are bonded at the bond areas on the cover strips to a confronting surface of the wrapper so that when the first and the second ends of the wrapper are pulled apart to open the wrapper and remove the bandage, each cover strip is peeled away from the bandage by a part of the wrapper to which the strip is bonded by the adhesive at the bond area on the strip, thus exposing the wound dressing pad for application on the wound and avoiding contact between the pad and a hand of a user.

2. An adhesive bandage wrapper construction according to claim 1, wherein the wrapper has a mark or other indicia located along the longitudinal edge between the first and the second ends of the wrapper, for indicating a position at which the wrapper separates when the first and the second ends of the wrapper are pulled apart to open the wrapper.

3. An adhesive bandage wrapper construction according to claim 1, wherein a portion of at least one of the first and the second cover strips overlaps the wound dressing pad on the bandage.

4. An adhesive bandage wrapper construction according to claim 1, wherein each one of the cover strips has a portion that folds back and over a portion of the strip in the region of the wound dressing pad to form corresponding folded portions of the strips, and each one of the folded portions of the strips is bonded by the adhesive at the bond area on the strip to a confronting surface of the wrapper.

5. An adhesive bandage wrapper construction according to claim 2, wherein the mark or other indicia along the longitudinal edge of the wrapper is a tear mark along which the wrapper is to be torn by hand by a user before the user pulls the ends of the wrapper apart to open the wrapper.

6. An adhesive bandage wrapper construction according to claim 2, wherein the mark or other indicia along the longitudinal edge of the wrapper is a slit.

7. An adhesive bandage wrapper construction according to claim 2, wherein the mark or other indicia along the longitudinal edge of the wrapper is a notch.

8. An adhesive bandage wrapper construction according to claim 1, wherein the bond areas on the cover strips are sufficiently spaced apart so that the wrapper separates in a region between the bond areas on the strips when the ends of the wrapper are pulled apart to open the wrapper.

9. The bandage wrapper construction of claim 1, wherein the adhesive in the bond areas on the cover strips is selected from a group comprising pressure-sensitive adhesives including rubbers, acrylate and silicone formulations; dissolvable adhesives; removable adhesives; reactive adhesives; drying adhesives; contact adhesives; light-curing adhesives; thermoplastic adhesives; synthetic adhesives including acrylics, cynoacrylates, silicone, and polyurethane; biological adhesives; and the like.

10. An adhesive bandage wrapper construction, comprising:
    a wrapper having a longitudinal edge between a first end and a second end of the wrapper;
    a bandage contained in the wrapper and including first and second adhesive areas on corresponding end portions of the bandage for adhering the bandage to a user's skin, and a wound dressing pad disposed between the first and the second adhesive areas for application on a wound of the user;
    a first cover strip and a second cover strip wherein the cover strips are substantially the same length, and each cover strip has a protective portion disposed to protect a corresponding adhesive area on the bandage;
    wherein the wrapper envelopes the bandage including the first and the second cover strips, and the cover strips are bonded to a confronting surface of the wrapper so that when the first and the second ends of the wrapper are pulled apart to open the wrapper and remove the bandage, each cover strip is peeled away from the bandage by a part of the wrapper to which the strip is bonded, thus exposing the wound dressing pad for application on the wound and avoiding contact between the pad and a hand of a user;
    each one of the cover strips has a portion that folds back and over a portion of the strip in the region of the wound dressing pad to form corresponding folded portions of the strips, and each one of the folded portions of the strips is bonded to a confronting surface of the wrapper;
    the folded portion of each cover strip is approximately one-half the length of the protective portion of the strip; and
    wherein the folded portions of the cover strips partially overlap one another.

* * * * *